United States Patent [19]

D'Alessio et al.

[11] Patent Number: 6,071,947
[45] Date of Patent: Jun. 6, 2000

[54] INDOLYL-PYRROLYDENEMETHYLPYRROLE DERIVATIVES AND PROCESS FOR THEIR PREPARATION

[75] Inventors: Roberto D'Alessio, Cinisello Balsamo; Marcellino Tibolla, Senago; Alberto Bargiotti, Milan; Anna Maria Isetta, Rho; Mario Ferrari; Francesco Colotta, both of Milan, all of Italy

[73] Assignee: Pharmacia & Upjohn S.p.A., Milan, Italy

[21] Appl. No.: 09/147,249

[22] PCT Filed: Feb. 27, 1998

[86] PCT No.: PCT/EP98/01285

§ 371 Date: Nov. 12, 1998

§ 102(e) Date: Nov. 12, 1998

[87] PCT Pub. No.: WO98/40380

PCT Pub. Date: Sep. 17, 1998

[30] Foreign Application Priority Data

Mar. 11, 1997 [GB] United Kingdom .................. 9705035

[51] Int. Cl.[7] .................. A61K 31/4025; A61K 31/405; C07D 207/333; C07D 209/12; C07D 403/14

[52] U.S. Cl. .................. 514/414; 514/415; 514/422; 514/427; 544/32; 544/34; 544/143; 546/81; 546/84; 546/201; 546/208; 548/490; 548/523; 548/524

[58] Field of Search ...................... 514/414, 415, 514/422, 427; 548/490, 523, 524

[56] References Cited

U.S. PATENT DOCUMENTS

| | | | |
|---|---|---|---|
| 5,607,960 | 3/1997 | Wythes | 514/414 |
| 5,691,334 | 11/1997 | Doria et al. | 514/235.5 |
| 5,847,127 | 12/1998 | D'Alessio et al. | 544/141 |

*Primary Examiner*—Johann Richter
*Assistant Examiner*—Jane C. Oswecki
*Attorney, Agent, or Firm*—Oblon, Spivak, McClelland, Maier & Neustadt, P.C.

[57] ABSTRACT

The present invention relates to substituted (1H-indol-2-yl)-5[(2H-pyrrol-2-ylidene) methyl]-1H-pyrrole compounds and their use as immunomodulating agents, to the preparation of the compounds and to pharmaceutical compositions comprising them.

18 Claims, No Drawings

INDOLYL-PYRROLYDENEMETHYLPYRROLE DERIVATIVES AND PROCESS FOR THEIR PREPARATION

This application is a 371 of PCT/EP98/01285 filed Feb. 27, 1998.

The present invention relates to new indolyl-pyrrolydenemethylpyrrole derivatives and their use as therapeutic agents, e.g. as immunomodulating agents, in particular as immunosuppressive agents, to a process for their preparation and to pharmaceutical compositions comprising them.

Presently, cyclosporin A, an immunosuppressive agent, used in combination with other adjunctive therapies, such as azathioprine and corticosteroids, is the treatment of choice for the prevention of organ transplantation rejection.

Other immunosuppressive agents such as FK506, mycophenolate mofetil, and rapamycin, have been used or have been suggested to be useful in the treatment and/or prevention of organ transplantation rejection.

Use of any of these known immunosuppressive compounds, either alone or in combination, is associated with a high incidence of side effects such as nephrotoxicity and/or hepatotoxicity. Thus, there presently exists a need for improved therapies to replace or to be used in combination with cyclosporin or other currently known immunosuppressive drugs for the treatment and/or prevention of organ transplantation rejection, graft versus host disease, autoimmune diseases, and chronic inflammatory diseases, including but not limited to psoriasis and rheumatoid arthritis.

The indolyl-pyrrolydenemethylpyrrole compounds of the present invention are useful as single therapy agents as well as in combination with other compounds currently used in these clinical regimens such as cyclosporin. In view of their biological properties the compounds of the present invention should be useful to permit the administration of reduced doses of other immunosuppressive agents used in combination therewith, thereby reducing the adverse effects of these agents.

Object of the present invention are new 2-(1H-indol-2-yl)-5[(2H-pyrrol-2-ylidene)methyl]-1H-pyrrole compounds having the following formula (I)

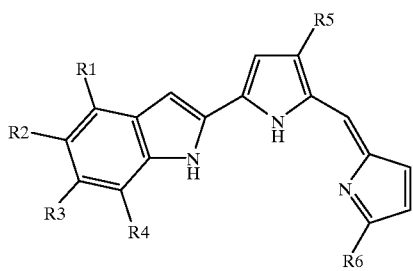

(I)

wherein
each of R1, R2, R3 and R4, which are the same or different, independently represents hydrogen, $C_1$–$C_6$ alkyl, halogen, cyano, nitro, hydroxy, $C_1$–$C_6$ alkoxy unsubstituted or substituted by phenyl, $C_1$–$C_6$ alkylcarbonyloxy, —NRaRb in which each of Ra and Rb independently is hydrogen or $C_1$–$C_6$ alkyl, $C_1$–$C_6$ alkyl-carbonylamino, carboxy, ($C_1$–$C_6$ alkoxy) carbonyl, aralkyl-carbamoyl, arylcarbamoyl or —CONRcRd in which each of Rc and Rd independently is hydrogen or $C_1$–$C_6$ alkyl or Rc and Rd, taken together with the nitrogen atom to which they are linked, form a morpholino or piperidino ring;

R5 represents halogen, hydroxy or $C_1$–$C_{11}$ alkoxy unsubstituted or substituted by phenyl; and R6 represents hydrogen, $C_2$–$C_{20}$ alkanoyl, $C_3$–$C_{20}$ alkenoyl, phenyl, $C_1$–$C_{20}$ alkyl or $C_2$–$C_{20}$ alkenyl, wherein the alkanoyl, alkenoyl, alkyl and alkenyl groups are unsubstituted or substituted by 1 to 3 substituents chosen independently from halogen, $C_1$–$C_6$ alkoxy, hydroxy, aryl, aryloxy, cyano, carboxy, ($C_1$–$C_6$ alkoxy)carbonyl, ($C_3$–$C_4$ alkenyl)carbamoyl, aralkyl-carbamoyl, arylcarbamoyl and —CONRcRd wherein Rc and Rd are as defined above;

and the pharmaceutically acceptable salts thereof.

The present invention includes within its scope all possible isomers, stereoisomers and optical isomers and their mixtures, and the metabolites and the metabolic precursors or bioprecursors of the compounds of formula (I).

The compounds of the invention can be represented also by the following tautomeric formula (Ia)

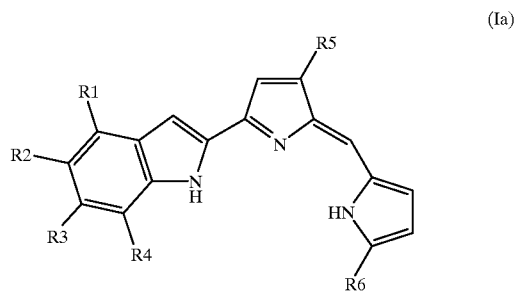

(Ia)

wherein
R1, R2, R3, R4, R5 and R6 are as defined above.

Accordingly, the chemical compounds provided by the present invention are named throughout the description of the invention according to the chemical nomenclature provided for the compounds of either formula (I) or (Ia), on the basis of the structural evidence validated by people skilled in the art.

A halogen atom is preferably chlorine or fluorine. The alkyl, alkoxy, alkenyl, alkanoyl, alkenoyl, alkadienoyl and alkylidene groups may be branched or straight chain groups.

An aryl group as a substituent as well as a moiety in an aryloxy, aralkyl or arylcarbamoyl group is, e.g., an aromatic $C_6$–$C_{20}$ mono- or poly-nuclear moiety, typically phenyl, unsubstituted or substituted by one or two substituents independently chosen from halogen, hydroxy, $C_1$–$C_6$ alkyl and $C_1$–$C_6$ alkoxy.

Accordingly an aralkyl group is e.g. benzyl or phenethyl, in which the phenyl ring is optionally substituted by one or two substituents independently chosen from halogen, hydroxy, $C_1$–$C_6$ alkyl and $C_1$–$C_6$ alkoxy.

A $C_3$–$C_4$ or C3–C6 alkenyl group is preferably an allyl group.

A $C_1$–$C_6$ alkyl group is preferably a $C_1$–$C_4$ alkyl group, in particular a methyl or ethyl group.

An unsubstituted $C_1$–$C_{11}$ alkoxy group is preferably a $C_1$–$C_4$ alkoxy or $C_8$–$C_{11}$ alkoxy group, typically methoxy, ethoxy, propoxy, butoxy and undecyloxy.

A $C_1$–$C_6$ alkoxy group substituted by phenyl is preferably a phenyl-$C_1$–$C_4$ alkoxy group, typically benzyloxy or phenylethoxy.

The acyl moiety in a $C_1$–$C_6$ alkyl-carbonyloxy and in a $C_1$–$C_6$ alkyl-carbonylamino group is e.g. $C_2$–$C_5$ alkanoyl, typically acetyl.

A $C_1$–$C_{20}$ alkyl group is preferably a $C_1$–$C_{14}$ alkyl group, in particular an undecyl group.

A $C_2$–$C_{20}$ alkenyl group is preferably a $C_5$–$C_{14}$ alkenyl group, in particular an undecenyl group.

A $C_2$–$C_{20}$ alkanoyl group is preferably a $C_5$–$C_{14}$ alkanoyl group, in particular an undecanoyl group.

A $C_3$–$C_{20}$ alkenoyl group is preferably a $C_5$–$C_{14}$ alkenoyl group, in particular an undecenoyl group.

A ($C_1$–$C_6$ alkoxy)carbonyl group is preferably a ($C_1$–$C_4$ alkoxy)carbonyl group, typically methoxycarbonyl or ethoxycarbonyl.

A $C_1$–$C_6$ alkyl-carbonylamino group is e.g. a $C_1$–$C_4$ alkyl-carbonylamino group, typically acetylamino or propionylamino.

Examples of pharmaceutically acceptable salts of the compounds of the invention are either those with inorganic bases, such as sodium, potassium, calcium and aluminium hydroxides, or with organic bases, such as lysine, arginine, N-methyl-glucamine, triethylamine, triethanolamine, dibenzylamine, methylbenzylamine, di-(2-ethyl-hexyl)-amine, piperidine, N-ethylpiperidine, N,N-diethylaminoethylamine, N-ethylmorpholine, β-phenethylamine, N-benzyl-β-phenethylamine, N-benzyl-N,N-dimethylamine and the other acceptable organic amines, as well as the salts with inorganic, e.g. hydrochloric, hydrobromic and sulphuric acids and with organic acids, e.g. citric, tartaric, maleic, malic, fumaric, methanesulphonic and ethanesulphonic acids.

As stated above, the present invention also includes within its scope pharmaceutically acceptable bio-precursors (otherwise known as pro-drugs) of the compounds of formula (I), i.e. compounds which have a different formula to formula (I) above, but which nevertheless upon administration to a human being are converted directly or indirectly in vivo into a compound of formula (I).

Preferred compounds of the invention are those wherein, in formula (I), each of R1, R2, R3 and R4 independently represents hydrogen, $C_1$–$C_4$ alkyl, halogen, cyano, nitro, hydroxy, $C_1$–$C_4$ alkoxy unsubstituted or substituted by phenyl, amino, carboxy, ($C_1$–$C_4$ alkoxy)carbonyl or CONRcRd in which each of Rc and Rd independently is hydrogen or $C_1$–$C_4$ alkyl or Rc and Rd, taken together with the nitrogen atom to which they are linked, form a morpholino or piperidino ring;

R5 represents hydroxy or $C_1$–$C_{11}$ alkoxy unsubstituted or substituted by phenyl; and R6 represents hydrogen, $C_1$–$C_{14}$ alkyl or $C_3$–$C_{14}$ alkenyl, wherein the alkyl and alkenyl groups are unsubstituted or substituted by a substituent chosen from halogen, $C_1$–$C_4$ alkoxy, hydroxy, aryl, aryloxy, cyano, carboxy, ($C_1$–$C_4$ alkoxy)carbonyl, aralkylcarbamoyl, arylcarbamoyl and —CONRcRd in which each of Rc and Rd independently is hydrogen or $C_1$–$C_4$ alkyl or Rc and Rd, taken together with the nitrogen atom to which they are linked, form a morpholino or piperidino ring.

Examples of specific preferred compounds of the invention are:

2-(1H-indol-2-yl)-4-methoxy-5-[(5-undecyl-2H-pyrrol-2-ylidene)methyl]-1H-pyrrole;
2-(1H-indol-2-yl)-4-methoxy-5-[(5-methyl-2H-pyrrol-2-ylidene)methyl]-1H-pyrrole;
2-(1H-indol-2-yl)-4-benzyloxy-5-[(5-methyl-2H-pyrrol-2-ylidene)methyl]-1H-pyrrole;
2-(1H-indol-2-yl)-4-methoxy-5-[(5-pentyl-2H-pyrrol-2-ylidene)methyl]-1H-pyrrole;
2-(1H-indol-2-yl)-4-benzyloxy-5-[(5-pentyl-2H-pyrrol-2-ylidene)methyl]-1H-pyrrole;
2-(1H-indol-2-yl)-4-methoxy-5-[(5-ethyl-2H-pyrrol-2-ylidene)methyl]-1H-pyrrole;
2-(1H-indol-2-yl)-4-methoxy-5-[(5-propyl-2H-pyrrol-2-ylidene)methyl]-1H-pyrrole;
2-(1H-indol-2-yl)-4-methoxy-5-[(5-isopropyl-2H-pyrrol-2-ylidene)methyl]-1H-pyrrole;
2-(1H-indol-2-yl)-4-methoxy-5-[(5-butyl-2H-pyrrol-2-ylidene)methyl]-1H-pyrrole;
2-(1H-indol-2-yl)-4-benzyloxy-5-[(5-ethyl-2H-pyrrol-2-ylidene)methyl]-1H-pyrrole;
2-(1H-indol-2-yl)-4-benzyloxy-5-[(5-propyl-2H-pyrrol-2-ylidene)methyl]-1H-pyrrole;
2-(1H-indol-2-yl)-4-benzyloxy-5-[(5-isopropyl-2H-pyrrol-2-ylidene)methyl]-1H-pyrrole;
2-(1H-indol-2-yl)-4-benzyloxy-5-[(5-butyl-2H-pyrrol-2-ylidene)methyl]-1H-pyrrole;
2-(5-methoxy-1H-indol-2-yl)-4-methoxy-5-[(5-undecyl-2H-pyrrol-2-ylidene)methyl]-1H-pyrrole;
2-(5-methoxy-1H-indol-2-yl)-4-benzyloxy-5-[(5-methyl-2H-pyrrol-2-ylidene)methyl]-1H-pyrrole;
2-(5-chloro-1H-indol-2-yl)-4-methoxy-5-[(5-undecyl-2H-pyrrol-2-ylidene)methyl]-1H-pyrrole;
2-(5-chloro-1H-indol-2-yl)-4-benzyloxy-5-[(5-methyl-2H-pyrrol-2-ylidene)methyl]-1H-pyrrole;
2-(5-cyano-1H-indol-2-yl)-4-methoxy-5-[(5-undecyl-2H-pyrrol-2-ylidene)methyl]-1H-pyrrole;
2-(5-cyano-1H-indol-2-yl)-4-benzyloxy-5-[(5-methyl-2H-pyrrol-2-ylidene)methyl]-1H-pyrrole;
2-(5-hydroxy-1H-indol-2-yl)-4-methoxy-5-[(5-undecyl-2H-pyrrol-2-ylidene)methyl]-1H-pyrrole;
2-(5-hydroxy-1H-indol-2-yl)-4-benzyloxy-5-[(5-methyl-2H-pyrrol-2-ylidene)methyl]-1H-pyrrole;
2-(5-amino-1H-indol-2-yl)-4-methoxy-5-[(5-undecyl-2H-pyrrol- 2-ylidene)methyl]-1H-pyrrole;
2-(5-amino-1H-indol-2-yl)-4-benzyloxy-5-[(5-methyl-2H-pyrrol-2-ylidene)methyl]-1H-pyrrole;
2-(5-methyl-1H-indol-2-yl)-4-methoxy-5-[(5-undecyl-2H-pyrrol-2-ylidene)methyl]-1H-pyrrole;
2-(5-benzyloxy-1H-indol-2-yl)-4-methoxy-5-[(5-undecyl-2H-pyrrol-2-ylidene)methyl]-1H-pyrrole;
2-(5-fluoro-1H-indol-2-yl)-4-methoxy-5-[(5-undecyl-2H-pyrrol-2-ylidene)methyl]-1H-pyrrole;
2-(5-carboxy-1H-indol-2-yl)-4-methoxy-5-[(5-undecyl-2H-pyrrol-2-ylidene)methyl]-1H-pyrrole;
2-(5-carbamoyl-1H-indol-2-yl)-4-methoxy-5-[(5-undecyl-2H-pyrrol-2-ylidene)methyl]-1H-pyrrole;
2-(6-carboxy-1H-indol-2-yl)-4-methoxy-5-[(5-undecyl-2H-pyrrol-2-ylidene)methyl]-1H-pyrrole;
2-(6-carbamoyl-1H-indol-2-yl)-4-methoxy-5-[(5-undecyl-2H-pyrrol-2-ylidene)methyl]-1H-pyrrole;
2-(6-nitro-1H-indol-2-yl)-4-methoxy-5-[(5-undecyl-2H-pyrrol-2-ylidene)methyl]-1H-pyrrole;
2-(7-ethyl-1H-indol-2-yl)-4-methoxy-5-1(5-undecyl-2H-pyrrol-2-ylidene)methyl]-1H-pyrrole; and the $C_1$–$C_6$ alkyl esters thereof, in particular the methyl and ethyl esters, and the pharmaceutically acceptable salts thereof, in particular the hydrochlorides, hydrobromides and methane-sulfonates.

A further object of the present invention is to provide a compound of formula (I), as defined above, for use in a method of treatment of the human or animal body by therapy, in particular as an immunomodulating agent, especially as an immunosuppressive agent.

Object of the present invention is also to provide a pharmaceutical composition comprising a pharmaceutically acceptable carrier and/or diluent and as an active principle a compound of formula (I), as herein defined, or a pharmaceutically acceptable salt thereof.

The present invention also provides the use of a compound of formula (I), as defined above, in the preparation of a medicament having immunomodulating, in particular immunosuppressive, activity.

The present invention also provides a method of treating a mammal, including humans, in need of an immunomodulating agent, said method comprising administering to said mammal an effective amount of a compound of formula (I), as herein defined, or a pharmaceutically acceptable salt thereof. The compounds of formula (I) and the pharmaceutically acceptable salts thereof can be obtained by an analogy process.

According to a preferred embodiment of the invention a compound of formula (I) and the salts thereof can be prepared by a process comprising treating a compound of formula (II)

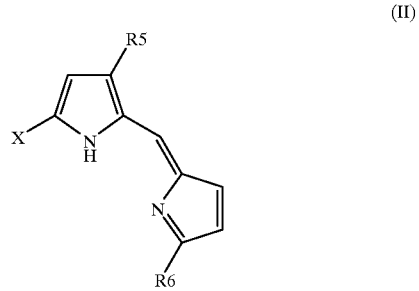

wherein
R5 and R6 are as defined above and X is a leaving group,
with a compound of formula (III)

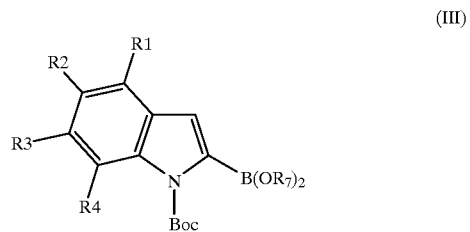

wherein
R1, R2, R3 and R4 are as defined above and R7 is hydrogen or a lower alkyl chain;
and, if desired, converting a compound of formula (I) into another compound of formula (I) and/or, if desired, salifying a compound of formula (I) and/or, if desired, converting a salt of a compound of formula (I) into a free compound and/or, if desired, separating a mixture of isomers of a compound of formula (I) into the single isomers.

When R7 is a lower alkyl chain, it is preferably a $C_1$–$C_4$ alkyl chain, for instance methyl, ethyl or isopropyl. In a compound of general formula (II), the leaving group X can be for instance a trifluoromethane-sulphonate group or a halogen such as chlorine, bromine or iodine.

The reaction between a compound of formula (II) and a compound of formula (III) may be carried out in a suitable organic solvent such as tetrahydofurane, dioxane, dimethoxyethane, DMF, toluene, methanol, ethanol water or mixtures thereof, in the presence of a suitable palladium (0) catalyst, in the presence of a basic agent, such as $K_2CO_3$, $Na_2CO_3$, $NaHCO_3$, $K_3PO_4$, NaOAc, KOH, NaOH, Ba(OH)$_2$, EtONa, Bu$_4$NF, Et$_3$N, at a temperature varying between about 60° C. and about 120° C., for a time of about 1 hour to about 3 days.

A wide range of palladium (0) catalysts can be used such as for instance Pd(PPh$_3$)$_4$, PdCl$_2$(PPh$_3$)$_2$, Pd(OAc)$_2$ plus PPh$_3$ or other ligands as described for example in Chem. Rev. 95, 2457 (1995).

Optionally, salt such as LiCl, LiBr, KCl, KBr can be added to stabilize the catalyst.

According to a preferred embodiment of the invention, when in a compound of formula (II) the leaving group X is trifluoromethanesulfonate, a preferred catalyst is Pd(PPh$_3$)$_4$ in the presence of sodium or potassium carbonate, and the reaction can be performed in dioxane or toluene, at a temperature varying between about 65° C. and about 90° C., for a time from about 5 hours to about 24 hours.

A compound of formula (I) may be converted, as stated above, into another compound of formula (I) by known methods. For example, in a compound of formula (I) a carboxy group may be converted into the corresponding ($C_1$–$C_6$ alkyl)- or arylcarbamoyl group by reaction with the suitable $C_1$–$C_6$ alkylamine or arylamine, respectively, in the presence of a suitable carbodiimide, such as dicyclohexyl-carbodiimide or 1-(3-dimethylamino-propyl)-3-ethyl-carbodiimide, in an inert solvent such as dichloromethane or tetrahydrofuran at a temperature varying between about 0° C. and about 30° C.

Also the optional salification of a compound of formula (I) as well as the conversion of a salt into the free compound and the separation of a mixture of isomers into the single isomers may be carried out by conventional methods. For example, the separation of optical isomers may be carried out by salification with an optically active base or acid and by subsequent fractional crystallization of the diastereoisomeric salts, followed by recovering of the optically active isomeric acids or, respectively, bases.

The compounds of formula (II) are novel compounds and are an object of the invention. A compound of formula (II) can be obtained from a compound of formula (IV)

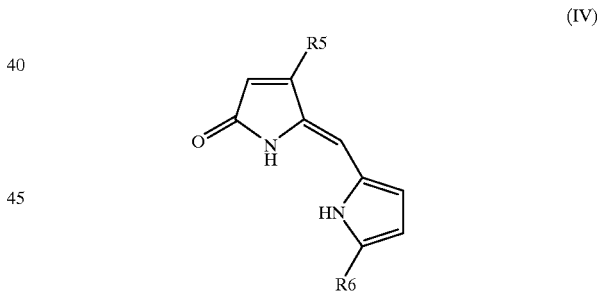

wherein
R5 and R6 are as defined above, by means of an opportune reagent such as for instance trifluoromethane-sulfonic anhydride or a halogenating agent such as POCl$_3$, POBr$_3$, POCl (OEt)$_2$/TMSI in an inert organic solvent such as dichloromethane, dichloroethane, acetonitrile, optionally in the presence of an organic base such as Et$_3$N or pyridine, at a temperature varying between about −20° C. and about 50° C.

The compounds of formula (III) are new and are a further object of this invention. They can be prepared starting from a suitable substituted indole as described in published procedures, as for instance in J. Org. Chem. 46, 157 (1981) and Synthesis, 613 (1991).

The compounds of formula (IV) are novel compounds and are a further object of the present invention. They can be prepared reacting a compound of formula (V)

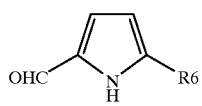
(V)

wherein
R6 is as defined above, with a compound of formula (VI)

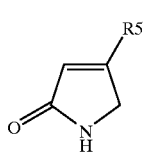
(VI)

wherein
R5 is as defined above.

The condensation between a compound of formula (V) and a compound of formula (VI) can be performed by acidic or basic catalysis, in a solvent such as water, methanol, ethanol, dioxane, THF, DMF, DMSO or mixtures thereof, at a temperature varying from about 25° C. to about 120° C., in a time ranging from about 1 hour to about 24 hours.

A acidic catalyst can be e.g. an inorganic acid such as HCl, HBr, $H_2SO_4$, $H_2NO_3$ or an organic acid such as, for instance, p-toluensulphonic acid, methansulphonic acid, trifluoromethan-sulphonic acid or trifluoroacetic acid.

As well, a basic catalyst can be e.g. an inorganic base such as NaOH, KOH, $K_2CO_3$, $Ba(OH)_2$, NaH or an organic base such as, for instance, t-BuOk, MeLi, BuLi, LDA.

A compound of formula (IV) can be also converted in another compound of formula (IV) having a different R3 alkoxy group using well known chemical procedures conventionally used for the transesterification of organic esters.

The compounds of formula (V) can be prepared, for example, by Vilsmeier formylation of the compounds of formula (VII)

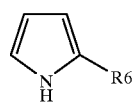
(VII)

wherein
R6 is as defined above, according to well known chemical procedures.

The compounds of formula (VII) are known compounds or may be prepared using mere variations of published procedures, for example those reported in the following chemical literature: Tetrahedron 32, 1851 (1976); J.Org.Chem. 53, 1410 (1988); J.Org.Chem. 28, 857 (1963); J.Am.Chem.Soc. 84, 4655 (1962); Ann. 450, 181 (1926); Ber. 99, 1414 (1966).

The compound of formula (VI) are commercially available or can be synthesized as described for example in Synthesis, 391 (1992) and Tetrahedron Letters 25, 1871 (1984).

A compound of formula (VI) can be converted in another compound of formula (VI) having a different R3 alkoxy group, using well known chemical procedures conventionally used for the transesterification of organic esters.

When in the compounds of formula (I) and in the intermediate products thereof, groups are present, such as COOH and/or OH, which need to be protected before submitting them to the hereabove illustrated reactions, they may be protected before the reactions take place and then deprotected, according to well known methods in organic chemistry.

The compounds of formula (I) and the pharmaceutically acceptable salts thereof are herein defined as the "compounds of the present invention", the "compounds of the invention" and/or the "active principles of the pharmaceutical compositions of the invention".

Pharmacology

The compounds of the invention have immunomodulating, in particular immunosuppressive, activity as found in several biological tests.

For instance, the compounds of the present invention have been evaluated on the following tests:

1. Proliferation of murine splenocytes induced by the mitogen Concanavaline A;
2. Proliferation of murine splenocytes induced by irradiated allogenic murine spleen cells (MLR);
3. Proliferation of tumor cell lines (human erythroleukemia K562, murine melanoma B16);
4. "Delayed-Type Hypersensitivity" assay;
5. Bioavailability after oral administration; and have been found to be very active and specific immunosuppressive agents.

Tests 1 and 2 allow the study of the compounds on proliferation models mediated by T-cell growth factors (e.g. IL-2) and are considered immunologically specific.

Test 3 allows to investigate the inhibitory effect of the present compounds on a generic proliferation pathway, independent of immune-specific growth factors.

Test 4 shows the T-lymphocyte mediated activity. The tests have been carried out as follows:

Test n° 1

Spleens were aseptically removed from C57B1/6 mice and a cell suspension prepared in complete medium. Cell viability was evaluated by trypan blue exclusion.

Spleen cells ($4\times10^5$) were cultured in triplicate in a volume of 0.15 ml, in flat bottomed microculture plates, in the absence or presence of an optimal concentration of ConA (1.7 microgr/ml) and of different concentrations of the test compound. Cultures were incubated for 72 h at 37° C. in a humidified, 5% $CO_2$ incubator; 18 h before termination of the cultures, 0.2 microCi of [methyl-$^3$H] thymidine were added to each well. Cells were harvested on glass fiber filters and the [$^3$H]TdR uptake (cpm) quantified in a liquid scintillation counter.

Test n° 2

Spleens were aseptically removed from C57B1/6 mice (responders) and Balb/c mice (stimulators), and cell suspensions prepared in complete medium. Responder cells ($1\times10^6$) were cocultured in triplicate with irradiated (1500R) stimulator cells ($5\times10^5$) in a volume of 0.15 ml in the presence or absence of different concentrations of the test compound, in flat bottomed microculture plates. Cultures were incubated for 96 h at 37° C. in a humidified, 5% $CO_2$ incubator; the last 18 h in the presence of 0.2 microCi of $^3$H-TdR.

Cells were harvested on glass fiber filter and the $^3$H-TdR uptake (cpm) quantified in a liquid scintillation counter.

Test n° 3

Tumor cells were collected in the logarithmic phase of growth and seeded in triplicate in flat bottomed microculture plates at the concentration of $1\times10^4$ in the presence or absence of different concentrations of the test compound.

After 48 h incubation at 37° C. in 5% CO$_2$, the cell viability was evaluated by the MTT colorimetric method according to Ferrari et al., J. Immunol. Methods (1990) 131, 165–72.

Test n° 4

Comparative in Vivo Activity Evaluation by DTH Assay

The immunosuppressive activity of the compounds of the invention was evaluated in vivo by DTH (Delayed-Type Hypersensitivity) assay. According to the test, sheep red blood cells (SRBC) (1×10$^5$ cells) suspended in 500 mcL saline, were injected i.v. into the tail vein of female C57 B1/6 mice (8–9 week old). Five days later 1×10$^8$ SRBC suspended in 50 mcL saline were injected into the left hind footpad. The increase in footpad thickness was measured with a dial micrometer 24 h after challenge. The test compounds were given daily for six days at different doses starting on the day of priming. Activity was expressed as ED30 (dose able to reduce by 30% the thickness increase compared to controls).

Test n° 5

In Vivo Bioavailability Evaluation

Aim of the study is to determine the pharmacokinetics and the oral bioavailability of the instant compounds in rats.

Species/strain/sex: rat/Lewis/male

No. formulations: 1 oral; 1 intravenous

No. animals/formulation: 3+2 controls (+an ulterior rat treated with the iv formulation); total 9

Dosages: iv: 1 mg salt/kg; oral: 10 mg salt/kg

Vehicles: iv: a solution at the conc. of 5 mg/ml in PEG 400/Tween 80 (6:1 v:v) was prepared, then diluted with dextrose at the final concentration of 0.5 mg/ml; oral: a solution at the concentration of 5 mg/ml in Cremophor ELP/EtOH abs (6.5:3.5 v:v) was prepared, then diluted with saline at the final concentration of 1 mg/ml Experimental: Three cannulated rats/formulation were treated. One rat/formulation was only treated with the vehicle, as basal sample. The intravenous administration was given into the caudal vein as bolus; the oral administration by gastric gavage as solution. Blood was withdrawn from the superior vena cava from each rat and collected into heparinized tubes at the following times: 2' (only for the iv route), 5', 15', 30'; 1, 2, 4, 6, 8, 24 and 32 h post-dosing. Plasma was immediately obtained by centrifugation (10000 rpm for 3 min) and stored in labelled tubes at −30° C. till analysis.

Analytical assay: the extraction of the compounds was performed by protein precipitation by adding 100 mcl of acetonitrile to 25 mcl of plasma. The concentrations of the compounds (as free bases) in plasma were determined by LC-MS method. Column: APEX CN RP 5 mc, 10×4 mm (Jones chromatography); mobil phase: 70% acetonitrile/30% 1 mM ammonium formate +0.01% triethylamine adjusted to pH 2.0 with formic acid; flow rate: 1 ml/min; injection volume: 10 mcL; oven temperature: 45° C.; MS detection by APCI using MRM positive ion; MRM transition: 330 m/z>239 m/z, retention time: 1.4 min; LLOQ: 5.03 ng/ml; ULOQ: 10060 ng/ml. Bioavailability is expressed in following Table 1 as F %.

Following Table 1 shows for instance the results obtained for four representative compounds of the invention in Test n° 4 and 5.

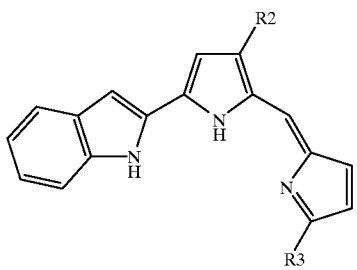

TABLE 1

| Compound | R2 | R3 | DTH ED30 (mg/kg) os | F % |
|---|---|---|---|---|
| PNU 190364 | CH$_3$O | C1 | 6.6 | 82 |
| PNU 190192 | CH$_3$O | C5 | 7.1 | 38 |
| PNU 190537 | BzO | C1 | 11.9 | 20 |
| PNU 166823 | CH$_3$O | C11 | 8.8 | 5 |

In Table 1:
PNU 190364 means 2-(1H-indol-2-yl)-4-methoxy-5-[(5-methyl-2H-pyrrol-2-ylidene)methyl]-1H-pyrrole, hydrochloride;
PNU 190192 means 2-(1H-indol-2-yl)-4-methoxy-5-[(5-pentyl-2H-pyrrol-2-ylidene)methyl]-1H-pyrrole, hydrochloride;
PNU 190537 means 2-(1H-indol-2-yl)-4-benzyloxy-5-[(5-methyl-2H-pyrrol-2-ylidene)methyl]-1H-pyrrole, hydrochloride; and
PNU 166823 means 2-(1H-indol-2-yl)-4-methoxy-5-[(5-undecyl-2H-pyrrol-2-ylidene)methyl]-1H-pyrrole, hydrochloride.

In view of their valuable biological properties the compounds of the invention can therefore be useful in mammals, including humans, as immunosuppressive agents for the prevention and treatment of rejection phenomena associated with tissue and organ transplantations, graft-versus-host diseases and autoimmune diseases. A mammal, comprising humans, in need of an immunomodulating agent, in particular of an immunosuppressive agent, can therefore be treated by a method comprising the administration thereto of a therapeutically effective amount of a compound of the invention or a pharmaceutically acceptable salt thereof. The condition of the human or animal patient can thus be improved.

Preferred cases of organ and tissue transplants which can be successfully treated by the compounds of the invention, hereabove described, are, for example, the cases of heart, kidney, bone marrow, lung, liver, and multiple organ transplantations.

Preferred cases of autoimmune diseases which can be successfully treated by the compounds of the invention, hereabove described, are for example, the cases of rheumatoid arthritis, systemic lupus erythematosus, juvenile diabetes, autoimmune haemolytic anaemia, miastenia gravis, multiple sclerosis, psoriasis, ulcerative colitis, idiopathic thrombocytopenic purpura, active chronic hepatitis, glomerulonephritis, idiopathic leucopenia, primary biliary cirrhosis, thyroiditis, thyrotoxicosis, dermatomyositis, discoid lupus erythematosus, psoriatic arthritis, regional enteritis, nephrotic syndrome, lupus nephritis, lupoid hepatitis, Sjogren's syndrome, Goodpasture's syndrome, Wegener's granulomatosis, scleroderma, Sezary's disease, uveitis and mumps orchitis. Typically rheumatoid arthritis, systemic lupus erythematosus, juvenile diabetes, miastenia gravis, multiple sclerosis and psoriasis.

The therapeutic regimen for the different clinical syndromes must be adapted to the type of pathology taking into account, as usual, also the route of administration, the form in which the compound is administered and the age, weight and conditions of the subject involved.

The oral route is employed, in general, for all conditions requiring such compounds. Preference is given to intravenous injection or infusion for the acute treatments.

For maintenance regimens the oral or parenteral, intramuscular or subcutaneous, route is preferred.

For these purposes the compounds of the invention, e.g. compound PNU 190364, can be administered orally at doses ranging e.g. from about 0.5 to about 10 mg/kg of body weight per day in adult humans.

Doses of active compounds ranging e.g. from about 0.25 to about 5 mg/kg of body weight per day can be used for the parenteral administration and for intravenous injection or infusion in adult humans. Of course, these dosage regimens may be adjusted to provide the optimal therapeutic response.

The nature of the pharmaceutical compositions containing the compounds of this invention in association with pharmaceutically acceptable carriers or diluents will, of course, depend upon the desired route of administration.

The compositions may be formulated in the conventional manner with the usual ingredients. For example, the compounds of the invention, may be administered in the form of aqueous or oily solutions or suspensions, tablets, pills, gelatine capsules, syrups, drops or suppositories.

Thus, for oral administration, the pharmaceutical compositions, containing the compounds of this invention, are preferably tablets, pills or gelatine capsules which contain the active substance together with diluents, such as lactose, dextrose, sucrose, mannitol, sorbitol, cellulose; lubricants, for instance silica, talc, stearic acid, magnesium or calcium stearate, and/or polyethylene glycols; or they may also contain binders, such as starches, gelatine, methylcellulose, carboxymethylcellulose, gum-arabic, tragacanth, polyvinylpyrrolidone; disaggregating agents, such as starches, alginic acid, alginates, sodium starch glycolate; effervescing mixture; dyestuffs; sweeteners; wetting agents, such as lecithin, polysorbates, laurylsulphates and in general, non-toxic and pharmacologically inactive substances used in pharmaceutical formulations.

Said pharmaceutical preparations may be manufactured in known manner, for example by means of mixing, granulating, tabletting, sugar-coating, or film-coating processes.

The liquid dispersions for oral administration may be e.g. syrups, emulsions and suspensions.

The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lidocaine hydrochloride.

The solutions for intravenous injections or infusions may contain as carrier, for example, sterile water or preferably they may be in the form of sterile aqueous isotonic saline solutions.

The suppositories may contain together with the active compound a pharmaceutically acceptable carrier, e.g. cocoabutter, polyethylene glycol, a polyoxyethylene sorbitan fatty acid ester surfactant or lecithin.

The present invention also provides products containing a compound of formula (I), or a pharmaceutically acceptable salt thereof, and an additional drug as a combined preparation for simultaneous, separate or sequential use in immunosuppressive therapy in mammals.

Such additional drug can be for instance a corticosteroid, an immunosuppressive or an anti-tumor agent, or mixtures of two or more of them.

The term "antitumor agent" is meant to comprise both a single anti-tumor drug and "cocktails", i.e a mixture of such drugs according to clinical practice.

Examples of anti-tumor agents that can be formulated with a compound of formula (I), include methotrexate and cyclophosphamide and mixtures thereof.

The term "immunosuppressive agent" is meant to comprise both a single immunosuppressive drug and "cocktails", i.e a mixture of such drugs according to clinical practice.

Examples of immunosuppressive agents that can be formulated with a compound of formula (I), include for instance one of the following:

cyclosporin A or cyclosporin C, a non-polar cyclic oligopeptide; FK506, a fungal macrolide immunosuppressive; azathioprine, or 6-[(1-Methyl-4-nitro-1H-imidazol-5-yl)-thio]1H-purine; methotrexate; rapamycin, a fungal macrolide immunosuppressive; mycophenolate mofetil, or 6-(4-hydroxy-6-methoxy-7-methyl-3-oxo-1,3-dihydroisobenzofuran-5-yl)-4-methyl-4-(E)-hexenoic acid 2-(4-morpholinyl)-ethyl ester; an immunosuppressive glucocorticoid, such as prednisone or dexamethasone; and/or polyclonal, such as a anti-human thymocite antibody or a monoclonal such as a anti-human CD3 antibody; or a mixture of two or more thereof.

It has to be noted that co-administration of an immunosuppressive agent, as defined above, and at least one compound of formula (I), or a pharmaceutically acceptable salt thereof, as herein defined, produces a potentiated immunosuppressive activity in synergistic way, thus giving a superadditive immunosuppressive effect, i.e. effect which is greater than the sum of the actions of the individual components. A person skilled in the art will appreciate that such superadditive immunosuppressive effect allows administration of lower dosage levels of immunosuppressive agents, thus lowering the side effects caused by commonly used immunosuppressant agents.

Accordingly, the present invention also provides a pharmaceutical composition for use in immunosuppressive therapy in mammals, including humans, comprising:

(a) an immunosuppressive agent in a pharmaceutically acceptable carrier and/or excipient, and (b) at least one compound of formula (I), as defined above, or a pharmaceutically acceptable salt thereof in a pharmaceutically acceptable carrier and/or excipient, in amounts to produce a superadditive immunosuppressant effect.

A further aspect of the present invention is an immunosuppressive therapy method for use in mammals, including humans, in need thereof, the method comprising administering to said mammal (a) an immunosuppressive agent and (b) at least one compound of formula (I), as defined above, or a pharmaceutically acceptable salt thereof, in amounts effective to produce a superadditive immunosuppressive effect.

In view of the combined therapeutic effect obtainable by such combined preparation, lower doses of immunosuppressive agents can thus be used.

Accordingly, the invention also provides a combination preparation comprising (a) an immunosuppressant agent and (b) at least one compound of formula (I), as defined above, or a pharmaceutically acceptable salt thereof, in a quantity effective to produce a superadditive immunosuppressive effect for use in a method for lowering the side effects caused by immunosuppressant therapy in mammals, including humans, in need thereof.

In the combined preparations, pharmaceutical compositions and method of treatment according to the present invention only one compound of formula (I), as defined above, or a pharmaceutically acceptable salt thereof, is preferably used. The combination preparation according to the invention can also include combination packs or compositions in which the constituents are placed side by side and can therefore be administered simultaneously, separately or sequentially to one and the same mammal, including humans.

The compounds of formula (I) and the pharmaceutically acceptable salts thereof have also been found to be active in treating adult-T-cell leukemia-lymphoma, in particular brought on by infection with HTLV-I in mammals, including humans. Such therapeutic activity of the compounds of the invention is proven for instance by the fact that they have been found to be active in inhibiting selectively the IL-2 induced activation and expansion of murine and human T-cells, showing thus a pharmacological profile consistent with the therapy of the IL-2 dependent ATL.

Inhibition of IL-2 Proliferation Induced Activity

The $Th_2$ murine cells D10-G4.1 (ATCC TIB 224) are IL-2 dependent for their growth. They are cultured in complete RPMI 1640 medium enriched with rhIL-2 (6 ng/ml) and ConA (6 ng/ml).

For testing the inhibitory effects of the compounds of the invention on IL-2 activity, D 10 cells are washed twice with complete medium, resuspended at $10^5$ cells/ml in the same medium and triplicately distributed ($10^4$ cells/well) in flat bottomed 96 well plates. 50 ml of rhIL-2 and 50 ml of the test compound at different concentrations are simultaneously added to the cells. The cultures are then incubated at 37° C. in a humidified 5% $CO_2$ incubator for 48 h, the last 18 h in the presence of 0.2 $\mu$Ci of $^3$H-TdR.

Uptake of 3H-TdR in the cells (cpm) is taken as a measure of cell proliferation.

For instance for the representative compound of the invention 2-(1H-indol-2-yl)-4-methoxy-5-[(5-pentyl-2H-pyrrol-2-ylidene)methyl]-1H-pyrrole (internal code PNU 190192) the following activity data were obtained.

| Compound | ng/ml | $^3$HTdR uptake * | % inhibition vs vehicle |
|---|---|---|---|
| PNU 190192 | 100 | 1388 (62) | 98 |
|  | 30 | 29681 (1528) | 52 |
|  | 10 | 57325 (1280) | 6 |
| vehicle | — | 61231 (1193) | — |

* mean cpm from triplicate wells (SE)

In treating a adult-T-cell leukemia-lymphoma one or more compound of formula (I), as defined above, can be administered alone or in association with an anti-tumor agent. Preferably a single compound of formula (I) is used. Accordingly, the present invention provides a compound of formula (I), as herein defined, or a pharmaceutically acceptable salt thereof for use in treating adult-T-cell leukemia-lymphoma.

A further object of the present invention is a method of treating mammals, including humans, suffering from adult-T-cell leukemia-lymphoma, said method comprising administering thereto a therapeutically effective amount of a compound of formula (I), as herein defined, or a pharmaceutically acceptable salt thereof.

Object of the present invention is also to provide a pharmaceutical composition having activity against adult-T-cell leukemia-lymphoma comprising a compound of formula (I), as herein defined, or a pharmaceutically acceptable salt thereof, as an active ingredient, and a pharmaceutically acceptable carrier or diluent.

A further object of the present invention is to provide a combined method of treatment of adult-T-cell leukemia-lymphoma in mammals, including humans, in need thereof, said method comprising administering thereto a compound of formula (I), or a pharmaceutically acceptable salt thereof, and an anti-tumor agent, in amounts and close enough together in time sufficient to produce a therapeutically useful effect. The present invention also provides a product containing a compound of formula (I), or a pharmaceutically acceptable salt thereof, and an anti-tumor agent as a combined preparation for simultaneous, separate or sequential use in adult-T-cell leukemia-lymphoma therapy.

The term "anti-tumor agent" is meant to comprise both a single anti-neoplastic agent and "cocktails", i.e. a mixture of such drugs according to clinical practice.

An anti-neoplastic agent in treating adult-T-cell leukemia lymphoma can be for example an agent selected from the group consisting of an antineoplastic vinca alkaloid, an antineoplastic antibiotic, an antineoplastic antimetabolite, an antineoplastic platinum coordination complex, an antineoplastic taxane compound, an antineoplastic ceramide compound, an antineoplastic distamycin compound, an antineoplastic epidophyllotoxin compound and an antineoplastic topoisomerase I inhibitor.

Examples of specific antineoplastic agents, according to the invention, which are administered with a compound of formula (I), are: vincristine, vinblastine, etoposide, tallimustine-amidoxime, 3-(1-methyl-4-(1-methyl-4-(1-methyl-4-(4,N, N-bis(2-chloroethyl)aminobenzene-1-carboxamido)pyrrole-2-carboxamido)pyrrole-2-carboxamido)pyrrole-2-carboxamido)proprionamidoxime, (2S-RR-4E)-1,3-dihydroxy-2-tetradecanoylamido-4-octadecene, paclitaxel, docetaxel, 7-epitaxol, 7-epitaxotere, epirubicin, doxorubicin, cyclophosphamide, idarubicin, 4'-iodoxorubicin, daunorubicin, actinomicin D, bleomycin, plycamicin, mitomycin, camptothecin, 9-aminocamptothecin, camptothecin 11 (CPT 11), topotecan, metotrexate, cytarabine, azauridine, azarabine, fluorodeoxyuridine, deoxycoformycin, mercaptopurine, cis-platin and carboplatin.

In particular they are epirubicin, doxorubicin, cyclophosphamide, 9-aminocamptothecin and camptothecin 11. The dosage of a compound of the invention to be administered to a patient suffering from adult-T-cell leukemia-lymphoma, in particular brought on by infection with HTLV-I, will vary with the precise nature of the conditions being treated and the recipient of the treatment.

A therapeutically effective dosage of the compounds of formula (I), for example the compound 2-(1H-indol-2-yl)-4-methoxy-5-[(5-pentyl-2H-pyrrol-2-ylidene)methyl]-1H-pyrrole, hydrochloride (PNU 190192), is in the range of about 0.03 to about 1.5 mg/kg, preferably about 0.06 mg/kg to about 0.7 mg/kg when given i.v. whereas the dose of the same compound for oral administration in adult humans is in general from about 0.3 mg/kg/day to about 15 mg/kg/day.

The dosage of a compound of formula (I) and of an antitumor agent, in case of combined therapy, to be used is, of course, dependent on various factors such as the organism to be treated (e.g., human or animal, age, weight, general state of health), the severity of the symptoms, the disorder to the accompanying treatment with other pharmaceuticals, or the frequency of the treatment. The dosages are in general administered several times per day and preferably once to three times per day. The effective amounts of the antitumor agent are in general those commonly used in therapy, as known to those skilled in the art. However, the amounts of the individual active compounds should be within the range given above, e.g. within the tolerable, efficacious dosage range for the organism to be treated.

The oral route is employed, in general, for all conditions requiring the compounds of the invention. Preference is given to intravenous injection or infusion for the acute treatments. For maintenance regimens the oral or parenteral, e.g. intramuscular or subcutaneous, route is preferred.

The nature of the pharmaceutical preparations and compositions according to the invention will of course depend upon the desired route of administration.

The compositions may be formulated in the conventional manner with the usual ingredients, for instance as described above.

The following examples illustrate but do not limit the invention.

EXAMPLE 1

Compound (IV)

To a solution of 2-formyl-5-undecylpyrrole (4 g; 16.03 mmols) and 4-methoxy-3-pyrrolin-2-one (3.63 g; 32.06 mmols) in DMSO (53 ml) 2N sodium hydroxyde (45 ml) is added under nitrogen atmosphere and the mixture is stirred at 60° C. for 8 hours. After dilution with water (200 ml) the yellow suspension is extracted with dichloromethane (600 ml). The organic phase is shaken with water and brine, anhydrified over anhydrous sodium sulphate and evaporated to dryness. The crude material is taken up in hexane and filtered to give 4-methoxy-5-(5-undecyl-1H-pyrrol-2-yl-methylene)-1,5-dihydro-pyrrol-2-one (4.86 g; 14.11 mmols) as a yellow crystalline solid. Yield: 88%.

$^1$NMR (400 mhz, CDCl$_3$), ppm:

0.87 (3H, m), 1.2–1.5 (16H, m), 1.72 (2H, m), 2.73 (2H, m), 3.89 (3H, s), 5.08 (1H, d, J=1.7 Hz), 5.97 (1H, dd, J=2.4 and 3.2 Hz), 6.31 (1H, s), 6.36 (1H, t, J=3.2 Hz), 10.25 (1H, bs), 10.74 (1H, bs).

EXAMPLE 2

Compound (II)

To a solution of 4-methoxy-5-(5-undecyl-1H-pyrrol-2-yl-methylene)-1,5-dihydro-pyrrol-2-one (1 g; 2.90 mmols) in dichloromethane (50 ml) at 0–5° C. trifluoromethansulphonic anhydride (0.586 ml; 3.48 mmols) is added dropwise under nitrogen atmosphere. After stirring at this temperature for 30' the reaction mixture is poured into a 2% NaHCO$_3$ solution and extracted with ethyl acetate (2×50 ml). The collected organic extracts are shaken with brine, anhydrified over anhydrous sodium sulphate and evaporated to dryness. The crude material is chromatographed on a short column of silica gel eluting with hexane/ethyl acetate 85/15 to give 2-trifluoromethansulphonyloxy-4-methoxy-5-[(5-undecyl-2H-pyrrol-2-ylidene)methyl]-1H-pyrrole (980 mg; 2.06 mmols) as a yellow solid. Yield: 71%.

$^1$NMR (400 mhz, CDCl$_3$), ppm:

0.88 (3H, m), 1.1–1.6 (16H, m), 1.68 (2H, m), 2.70 (2H, m), 3.88 (3H, s), 5.45 (1H, s), 6.08 (1H, d, J=4.0 Hz), 6.70 (1H, d, J=4.0 Hz), 7.05 (1H, s), 10.9 (1H, bs).

EXAMPLE 3

Interconversion Between Compounds (VI)

A solution of 4-methoxy-3-pyrrolin-2-one (3 g; 26.52 mmols) in absolute ethanol (60 ml) is treated with sodium ethoxyde (2.17 g; 31.82 mmols) under nitrogen atmosphere. The solution is refluxed for 2 hours and then poured into a 30% NaH$_2$PO$_4$ solution (200 ml). The resulting mixture is extracted with ethyl acetate (3×150 ml) and the organic phase is shaken with brine, dried over sodium sulphate and evaporated to dryness to obtain 4-ethoxy-3-pyrrolin-2-one (2.19 g; 17.24 mmols). Yield: 65%.

$^1$NMR (400 mhz, CDCl$_3$), ppm:

1.38 (3H, t), 3.89 (2H, s), 4.01 (2H, q), 5.03 (1H, s), 6.15 (1H, bs).

EXAMPLE 4

Interconversion Between Compounds (IV)

A solution of 4-methoxy-5-(5-undecyl-1H-pyrrol-2-yl-methylene)-1,5-dihydro-pyrrol-2-one (190 mg; 1 mmol) in amyl alcohol (4.75 ml) and dioxane (4.75 ml) is treated with 0.25 N methansulphonic acid in dioxane (1 ml) and stirred at room temperature under nitrogen atmosphere for 6 hours. The mixture is then poured into water (50 ml) and extracted with ethyl acetate (3×30 ml). The organic phase is shaken with brine, dried over sodium sulphate and evaporated to dryness. The crude material is purified on silica gel eluting with ethyl acetate/methanol 98/2 to give 4-amyloxy-5-(5-undecyl-1H-pyrrol-2-yl-methylene)-1,5-dihydro-pyrrol-2-one (110 mg; 0.45 mmols). Yield: 45%.

$^1$NMR (400 mhz, CDCl$_3$), ppm:

0.91 (6H, m), 1.2–1.5 (20H, m), 1.72 (2H, m), 1.82 (2H, m), 2.73 (2H, m), 4.01 (2H, t), 5.08 (1H, d, J=1.7 Hz), 5.99 (1H, dd, J=2.4 and 3.2 Hz), 6.30 (1H, s), 6.36 (1H, t, J=3.2 Hz), 10.30 (1H, bs), 10.75 (1H, bs).

EXAMPLE 5

Compound (III)

To a solution of 2,2,6,6-tetramethylpiperidine (11.0 g; 78 mmols) in THF (170 ml), at −78° C. and under nitrogen, a 1.6M solution of BuLi (56.1 ml; 89.7 mmols) in hexane is added slowly in order to maintain the temperature below −65° C. The mixture is stirred at −75° C. for 10 min and is then warmed to 0° C. within 30 min. After cooling again to −78° C., a solution of 1-tert-butoxycarbonylindole (15.6 g; 72 mmols) in THF (300 ml) is added, keeping the temperature below −65° C. The mixture is stirred 1 hour at −75° C. and a solution of trimrthyl borate (7.5 g; 72 mmols) in THF (200 ml) is added dropwise. The reaction is allowed to warm up to room temperature overnight. A 0.25N solution of Hcl (200 ml) is added and the THF is removed under vacuum. The residue is extracted with ethyl ether (3×150 ml) and the combined organic phases are washed with water (2×100 ml) and dried over sodium sulphate. The solution is then concentrated, cooled to 0° C. and filtered to obtain crystalline (1-tert-butoxycarbonylindol-2-yl)boronic acid (6.95 g; 26.6 mmols). Yield: 37%.

$^1$NMR (400 mhz, CDCl$_3$), ppm:

1.73 (9H, s), 7.31 (2H, m), 7.56 (2H, m), 7.57 (2H, bs) 8.01 (1H, bd, J=8.2 Hz).

EXAMPLE 6

Compound (I)

An oxygen free solution of 2-trifluoromethane-sulphonyloxy-4-methoxy-5-[(5-undecyl-2H-pyrrol-2- ylidene)methyl]-1H-pyrrole (418 mg; 0.877 mmols) in dioxane (30 ml) is treated in sequence, under argon atmosphere, with (1-t-butoxycarbonyl-indol-2-yl)boronic acid (916 mg; 3.51 mmols), potassium carbonate (969 mg; 7.02 mmols), tetrakis (triphenylphosphine)palladium(0) (50 mg; 0.044 mmols) and heated to 90° C., under stirring, for 6 hours. After cooling, the reaction mixture is poured into ice-water (100 ml) and extracted with ethyl acetate (3×50 ml). The organic phase is shaken with water and brine, anhydrified over anhydrous sodium sulphate, filtered and evaporated to dryness in vacuum. The residue is purified over a short $Al_2O_3$ column (activity II–III) using hexane/ethyl acetate 4/1 as eluant. The collected fractions are concentrated, treated with a solution of hydrochloric acid in isopropyl ether and evaporated to dryness in vacuum at room temperature to give 2-(1H-indol-2-yl)-4-methoxy-5-[(5-undecyl-2H-pyrrol-2-ylidene)methyl]-1H-pyrrole, hydrochloride (295 mg; 0.612 mmols), m.p. 92–95° C. Yield: 70%.

$^1$NMR (400 mhz, $CDCl_3$), ppm:

0.87 (3H, m), 1.1–1.9 (18H, m), 3.00 (2H, m), 4.06 (3H, s), 6.29 (1H, dd, J=1.7 and 4.1 Hz), 6.32 (1H, d, J=2 Hz), 6.95 (1H, dd, J=2.4 and 4.1 Hz), 7.0–7.4 (3H, m), 7.13 (1H, s), 7.61 (2H, m), 12.4 (1H, bs), 13.2 (1H, bs), 13.3 (1H, bs).

By Analogous Procedure the following Compounds can be Synthesized 2-(5-methoxy-1H-indol-2-yl)-4-methoxy-5-[(5-undecyl-2H-pyrrol-2-ylidene)methyl]-1H-pyrrole, hydrochloride $^1$NMR (400 mhz, $CDCl_3$), ppm:

0.85 (3H, m), 1.1–1.9 (18H, m), 2.97 (2H, m), 3.82 (3H, s), 4.03 (3H, s), 6.26 (2H, m), 6.91 (1H, dd, J=2.4 and 4.0 Hz), 6.97 (2H, m), 7.07 (2H, m), 7.47 (1H, m), 12.3 (1H, bs), 13.1 (1H, bs), 13.2 (1H, bs).

2-(1H-indol-2-yl)-4-methoxy-5-[(5-methyl-2H-pyrrol-2-ylidene)methyl]-1H-pyrrole, hydrochloride (PNU 190364)

$^1$NMR (400 mhz, $CDCl_3$), ppm:

2.65 (3H, s), 4.04 (3H, s), 6.23 (1H, dd, J=1.5, 4.0 Hz), 6.28 (1H, d, J=1.8 Hz), 6.91 (1H, dd, J=4, 2.5), 7.04 (1H, s), 7.10 (1H, m), 7.16 (1H, d, 1.5 Hz), 7.31 (1H, m), 7.58 (2H, m), 12.33 (1H, bs), 13.05 (1H, bs), 13.15 (1H, bs).

2-(1H-indol-2-yl)-4-benzyloxy-5-[(5-methyl-2H-pyrrol-2-ylidene)methyl]-1H-pyrrole, hydrochloride (PNU 190537)

$^1$NMR (400 mhz, $CDCl_3$), ppm:

2.66 (1H, s), 5.25 (2H, s), 6.25 (1H, dd, J=1.7, 3.9 Hz), 6.37 (1H, d, J=2.1 Hz), 6.94 (1H, dd, J=3.9, 2.5), 7.11 (1H, m), 7.16 (1H, s), 7.19 (1H, d, 1.7 Hz), 7.31 (1H, m) 7.4–7.5 (5H, m), 7.60 (2H, m).

2-(1H-indol-2-yl)-4-methoxy-5-[(5-pentyl-2H-pyrrol-2-ylidene)methyl]-1H-pyrrole, hydrochloride (PNU 190192)

$^1$NMR (400 mhz, $CDCl_3$), ppm:

0.91 (3H, t, J=7.2 Hz), 1.40 (4H, m), 1.81 (2H, m), 3.00 (2H, t, J=7.7 HZ), 4.05 (3H, s), 6.29 (1H, dd, J=1.8, 4.0 Hz), 6.30 (1H, d, J=1.8 Hz), 6.95 (1H, dd, J=2.6, 4.0 Hz), 7.11 (2H, m), 7.19 (1H, d, J=1.8 Hz), 7.31 (1H, m), 7.60 (2H, d, J=8.8 Hz), 12.39 (1H, bs), 13.14 (1H, bs), 13.22 (1H, bs).

2-(1H-indol-2-yl)-4-benzyloxy-5-[(5-pentyl-2H-pyrrol-2-ylidene)methyl]-1H-pyrrole, hydrochloride (PNU 169819)

$^1$NMR (400 mhz, $CDCl_3$), ppm:

0.91 (3H, t, J=7.2 Hz), 1.40 (4H, m), 1.81 (2H, m), 3.00 (2H, t, J=7.7 HZ), 5.26 (2H, s), 6.29 (1H, dd, J=1.8, 4.0 Hz), 6.37 (1H, d, J=1.8 Hz), 6.96 (1H, dd, J=2.5, 4.0 Hz), 7.11 (1H, m), 7.18 (2H, s), 7.31 (1H, m), 7.4–7.5 (5H, m) 7.60 (2H, m), 12.41 (1H, bs), 13.19 (1H, bs), 13.27 (1H, bs).

2-(1H-indol-2-yl)-4-methoxy-5-[(5-ethyl-2H-pyrrol-2-ylidene)methyl]-1H-pyrrole, hydrochloride;

2-(1H-indol-2-yl)-4-methoxy-5-[(5-propyl-2H-pyrrol-2-ylidene)methyl]-1H-pyrrole, hydrochloride;

2-(1H-indol-2-yl)-4-methoxy-5-[(5-isopropyl-2H-pyrrol-2-ylidene)methyl]-1H-pyrrole, hydrochloride;

2-(1H-indol-2-yl)-4-methoxy-5-[(5-butyl-2H-pyrrol-2-ylidene)methyl]-1H-pyrrole, hydrochloride;

2-(1H-indol-2-yl)-4-benzyloxy-5-[(5-ethyl-2H-pyrrol-2-ylidene)methyl]-1H-pyrrole, hydrochloride;

2-(1H-indol-2-yl)-4-benzyloxy-5-[(5-propyl-2H-pyrrol-2-5 ylidene)methyl]-1H-pyrrole, hydrochloride;

2-(1H-indol-2-yl)-4-benzyloxy-5-[(5-isopropyl-2H-pyrrol-2-ylidene)methyl]-1H-pyrrole, hydrochloride;

2-(1H-indol-2-yl)-4-benzyloxy-5-[(5-butyl-2H-pyrrol-2-ylidene)methyl]-1H-pyrrole, hydrochloride;

2-(5-methoxy-1H-indol-2-yl)-4-benzyloxy-5-[(5-methyl-2H-pyrrol-2-ylidene)methyl]-1H-pyrrole, hydrochloride;

2-(5-chloro-1H-indol-2-yl)-4-methoxy-S-l(5-undecyl-2H-pyrrol-2-ylidene)methyl]-1H-pyrrole, hydrochloride (PNU 169683)

$^1$NMR (400 mhz, $CDCl_3$), ppm:

0.87 (3H, t, J=7 Hz), 1.2–1.5 (16H, m), 1.8 (2H, m), 3.00 (2H, t, J=7.7 HZ), 4.05 (3H, s), 6.31 (2H, m), 6.98 (1H, dd, J=2.6, 4.0 Hz), 7.09 (1H, d, J=1.5 Hz), 7.13 (1H, s) 7.25 (1H, dd, J=2.2, 8.8 Hz), 7.51 (1H, d, J=8.8 Hz), 7.55 (1H, d, J=2.2 Hz), 12.50 (1H, bs), 13.14 (1H, bs), 13.21 (1H, bs).

2-(5-chloro-1H-indol-2-yl)-4-benzyloxy-5-[(5-methyl-2H-pyrrol-2-ylidene)methyl]-1H-pyrrole, hydrochloride;

2-(5-cyano-1H-indol-2-yl)-4-methoxy-5-[(5-undecyl-2H-pyrrol-2-ylidene)methyl]-1H-pyrrole, hydrochloride;

2-(5-cyano-1H-indol-2-yl)-4-benzyloxy-5-[(5-methyl-2H-pyrrol-2-ylidene)methyl]-1H-pyrrole, hydrochloride;

2-(5-hydroxy-1H-indol-2-yl)-4-methoxy-5-[(5-undecyl-2H-pyrrol-2-ylidene)methyl]-1H-pyrrole, hydrochloride;

2-(5-hydroxy-1H-indol-2-yl)-4-benzyloxy-5-[(5-methyl-2H-pyrrol-2-ylidene)methyl]-1H-pyrrole, hydrochloride;

2-(5-amino-1H-indol-2-yl)-4-methoxy-5-[(5-undecyl-2H-pyrrol-2-ylidene)methyl]-1H-pyrrole, dihydrochloride;

2-(5-amino-1H-indol-2-yl)-4-benzyloxy-5-[(5-methyl-2H-pyrrol-2-ylidene)methyl]-1H-pyrrole, dihydrochloride;

2-(5-methyl-1H-indol-2-yl)-4-methoxy-5-[(5-undecyl-2H-pyrrol-2-ylidene)methyl]-1H-pyrrole, hydrochloride;

2-(5-benzyloxy-1H-indol-2-yl)-4-methoxy-5-[(5-undecyl-2H-pyrrol-2-ylidene)methyl]-1H-pyrrole, hydrochloride;

2-(5-fluoro-1H-indol-2-yl)-4-methoxy-5-[(5-undecyl-2H-pyrrol-2-ylidene)methyl]-1H-pyrrole, hydrochloride;

2-(5-carboxy-1H-indol-2-yl)-4-methoxy-5-[(5-undecyl-2H-pyrrol-2-ylidene)methyl]-1H-pyrrole, hydrochloride;

2-(5-carboxy-1H-indol-2-yl)-4-methoxy-5-[(5-undecyl-2H-pyrrol-2-ylidene)methyl]-1H-pyrrole, methyl ester, hydrochloride;

2-(5-carbamoyl-1H-indol-2-yl)-4-methoxy-5-[(5-undecyl-2H-pyrrol-2-ylidene)methyl]-1H-pyrrole, hydrochloride;

2-(6-carboxy-1H-indol-2-yl)-4-methoxy-5-[(5-undecyl-2H-pyrrol-2-ylidene)methyl]-1H-pyrrole, hydrochloride;

2-(6-carboxy-1H-indol-2-yl)-4-methoxy-5-[(5-undecyl-2H-pyrrol-2-ylidene)methyl]-1H-pyrrole, methyl ester, hydrochloride;

2-(6-carbamoyl-1H-indol-2-yl)-4-methoxy-5-[(5-undecyl-2H-pyrrol-2-ylidene)methyl]-1H-pyrrole, hydrochloride;

2-(6-nitro-1H-indol-2-yl)-4-methoxy-5-[(5-undecyl-2H-pyrrol-2-ylidene)methyl]-1H-pyrrole, hydrochloride; and 2-(7-ethyl-1H-indol-2-yl)-4-methoxy-5-[(5-undecyl-2H-pyrrol-2-ylidene)methyl]-1H-pyrrole, hydrochloride.

EXAMPLE 7

Formulation: capsules (150 mg).

Capsules, each weighing 400 mg and containing 150 mg of the active substance, are manufactured as follows.

Composition:

| | |
|---|---|
| 2-(1H-indol-2-yl)-4-methoxy-5-[(5-undecyl-2H-pyrrol-2-ylidene)methyl]-1H-pyrrole, hydrochloride | 150 mg |
| Lactose | 198 mg |
| Corn starch | 50 mg |
| Magnesium stearate | 2 mg |
| Total | 400 mg |

Encapsulated in two-piece hard gelatin capsules.

What is claimed is:

1. A compound which is a (1H-indol-2-yl)-5[(2H-pyrrol-2-ylidene)methyl]-1H-pyrrole derivative of formula (I)

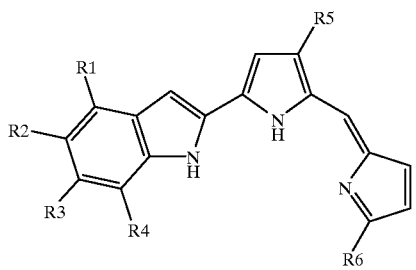

(I)

wherein
each of R1, R2, R3 and R4, which are the same or different, independently represents hydrogen, $C_1$–$C_6$ alkyl, halogen, cyano, nitro, hydroxy, $C_1$–$C_6$ alkoxy unsubstituted or substituted by phenyl, $C_1$–$C_6$ alkyl-carbonyloxy, —NRaRb in which each of Ra and Rb independently is hydrogen or $C_1$–$C_6$ alkyl, $C_1$–$C_6$ alkyl-carbonylamino, carboxy, ($C_1$–$C_6$ alkoxy) carbonyl, aralkyl-carbamoyl, arylcarbamoyl or —CONRcRd in which each of Rc and Rd independently is hydrogen or $C_1$–$C_6$ alkyl, or Rc and Rd, taken together with the nitrogen atom to which they are linked, form a morpholino or piperidino ring;

R5 represents halogen, hydroxy or $C_1$–$C_{11}$ alkoxy unsubstituted or substituted by phenyl; and R6 represents hydrogen, $C_2$–$C_{20}$ alkanoyl, $C_3$–$C_{20}$ alkenoyl, phenyl, $C_1$–$C_{20}$ alkyl or $C_2$–$C_{20}$ alkenyl, wherein the alkanoyl, alkenoyl, alkyl and alkenyl groups are each unsubstituted or substituted by 1 to 3 substituents chosen independently from halogen, $C_1$–$C_6$ alkoxy, hydroxy, aryl, aryloxy, cyano, carboxy, ($C_1$–$C_6$ alkoxy)carbonyl, ($C_3$–$C_4$ alkenyl)carbamoyl, aralkylcarbamoyl, arylcarbamoyl and —CONRcRd wherein Rc and Rd are as defined above;

or a pharmaceutically acceptable salt thereof.

2. A compound according to claim 1, wherein
each of R1, R2, R3 and R4 independently represents hydrogen, $C_1$–$C_4$ alkyl, halogen, cyano, nitro, hydroxy, $C_1$–$C_4$ alkoxy unsubstituted or substituted by phenyl, amino, carboxy, ($C_1$–$C_4$ alkoxy)carbonyl or CONRcRd in which each of Rc and Rd independently is hydrogen or $C_1$–$C_4$ alkyl or Rc and Rd, taken together with the nitrogen atom to which they are linked, form a morpholino or piperidino ring;

R5 represents hydroxy or $C_1$–$C_{11}$ alkoxy unsubstituted or substituted by phenyl; and R6 represents hydrogen, $C_1$–$C_4$ alkyl or $C_3$–$C_4$ alkenyl, wherein the alkyl and alkenyl groups are unsubstituted or substituted by a substituent chosen from halogen, $C_1$–$C_4$ alkoxy, hydroxy, aryl, aryloxy, cyano, carboxy, ($C_1$–$C_4$ alkoxy)carbonyl, aralkylcarbamoyl, arylcarbamoyl and —CONRcRd in which each of Rc and Rd independently is hydrogen or $C_1$–$C_4$ alkyl, or Rc and Rd, taken together with the nitrogen atom to which they are linked, form a morpholino or piperidino ring.

3. A compound selected from:
2-(1H-indol-2-yl)-4-methoxy-5-[(5-undecyl-2H-pyrrol-2-ylidene)methyl]-1H-pyrrole;
2-(1H-indol-2-yl)-4-methoxy-5-[(5-methyl-2H-pyrrol-2-ylidene)methyl]-1H-pyrrole;
2-(1H-indol-2-yl)-4-benzyloxy-5-[(5-methyl-2H-pyrrol-2-ylidene)methyl]-1H-pyrrole;
2-(1H-indol-2-yl)-4-methoxy-5-[(5-pentyl-2H-pyrrol-2-ylidene)methyl]-1H-pyrrole;
2-(1H-indol-2-yl)-4-benzyloxy-5-[(5-pentyl-2H-pyrrol-2-ylidene)methyl]-1H-pyrrole;
2-(1H-indol-2-yl)-4-methoxy-5-[(5-ethyl-2H-pyrrol-2-ylidene)methyl]-1H-pyrrole;
2-(1H-indol-2-yl)-4-methoxy-5-[(5-propyl-2H-pyrrol-2-ylidene)methyl]-1H-pyrrole;
2-(1H-indol-2-yl)-4-methoxy-5-[(5-isopropyl-2H-pyrrol-2-ylidene)methyl]-1H-pyrrole;
2-(1H-indol-2-yl)-4-methoxy-5-[(5-butyl-2H-pyrrol-2-ylidene)methyl]-1H-pyrrole;
2-(1H-indol-2-yl)-4-benzyloxy-5-((5-ethyl-2H-pyrrol-2-ylidene)methyl]-1H-pyrrole;
2-(1H-indol-2-yl)-4-benzyloxy-5-[(5-propyl-2H-pyrrol-2-ylidene)methyl]-1H-pyrrole;
2-(1H-indol-2-yl)-4-benzyloxy-5-[(5-isopropyl-2H-pyrrol-2-ylidene)methyl]-1H-pyrrole;
2-(1H-indol-2-yl)-4-benzyloxy-5-[(5-butyl-2H-pyrrol-2-ylidene)methyl]-1H-pyrrole;
2-(5-methoxy-1H-indol-2-yl)-4-methoxy-5-[(5-undecyl-2H-pyrrol-2-ylidene)methyl]-1H-pyrrole;
2-(5-methoxy-1H-indol-2-yl)-4-benzyloxy-5-[(5-methyl-2H-pyrrol-2-ylidene)methyl]-1H-pyrrole;
2-(5-chloro-1H-indol-2-yl)-4-methoxy-5-[(5-undecyl-2H-pyrrol-2-ylidene)methyl]-1H-pyrrole;
2-(5-chloro-1H-indol-2-yl)-4-benzyloxy-5-[(5-methyl-2H-pyrrol-2-ylidene)methyl]-1H-pyrrole;
2-(5-cyano-1H-indol-2-yl)-4-methoxy-30 2-ylidene) methyl]-1H-pyrrol-2-ylidene)methyl]-1H-pyrrole;
2-(5-cyano-1H-indol-2-yl)-4-benzyloxy-5-[(5-methyl-2H-pyrrol- 2-ylidene)methyl]-1H-pyrrole;
2-(5-hydroxy-1H-indol-2-yl)-4-methoxy-5-[(5-undecyl-2H-pyrrol-2-ylidene)methyl]-1H-pyrrole;
2-(5-hydroxy-1H-indol-2-yl)-4-benzyloxy-5-[(5-methyl-2H-pyrrol-2-ylidene)methyl]-1H-pyrrole;
2-(5-amino-1H-indol-2-yl)-4-methoxy-5-[(5-undecyl-2H-pyrrol-2-ylidene)methyl]-1H-pyrrole;
2-(5-amino-1H-indol-2-yl)-4-benzyloxy-5-[(5-methyl-2H-pyrrol-2-ylidene)methyl]-1H-pyrrole;
2-(5-methyl-1H-indol-2-yl)-4-methoxy-5-[(5-undecyl-2H-pyrrol-2-ylidene)methyl]-1H-pyrrole;
2-(5-benzyloxy-1H-indol-2-yl)-4-methoxy-5-[(5-undecyl-2H-pyrrol-2-ylidene)methyl]-1H-pyrrole;
2-(5-fluoro-1H-indol-2-yl)-4-methoxy-5-[(5-undecyl-2H-pyrrol-2-ylidene)methyl]-1H-pyrrole;
2-(5-carboxy-1H-indol-2-yl)-4-methoxy-5-(5-undecyl-2H-pyrrol-2-ylidene)methyl]-1H-pyrrole;
2-(5-carbamoyl-1H-indol-2-yl)-4-methoxy-5-[(5-undecyl-2H-pyrrol-2-ylidene)methyl]-1H-pyrrole;

2-(6-carboxy-1H-indol-2-yl)-4-methoxy-5-[(5-undecyl-2H-pyrrol-2-ylidene)methyl)]-1H-pyrrole;
2-(6-carbamoyl-1H-indol-2-yl)-4-methoxy-5-[(5-undecyl-2H-pyrrol-2-ylidene)methyl]-1H-pyrrole;
2-(6-nitro-1H-indol-2-yl)-4-methoxy-5-[(5-undecyl-2H-pyrrol-2-ylidene)methyl]-1H-pyrrole;
2-(7-ethyl-1H-indol-2-yl)-4-methoxy-5-[(5-undecyl-2H-pyrrol-2-ylidene)methyl]-1H-pyrrole; and the $C_1$–$C_6$ alkyl esters and pharmaceutically acceptable salts thereof.

4. A compound according to claim 3, in the form of a hydrochloride, hydrobromide or methanesulfonate salt.

5. A pharmaceutical composition comprising a pharmaceutically acceptable carrier and/or diluent and, as an active principle, a compound as defined in claim 1.

6. A compound as claimed in claim 1, for use as an immunomodulating agent or in the treatment of adult-T-cell leukemia-lymphoma.

7. A product containing a compound of formula (I) as defined in claim 1 and an additional drug as a combined preparation for simultaneous, separate or sequential use in immunosuppressive therapy in mammals.

8. A product according to claim 7, wherein the additional drug is an immunosuppressive agent selected from the group consisting of cyclosporin A, cyclosporin C, FD506, azathioprine, 6-1H-purine, methotrexate, rapamycin, mycophenolate mofetil, 6-(4-hydroxy-6-methoxy-7-methyl-3-oxo-1,3-dihydroisobenzofuran-5-yl)-4-methyl-4-(E)-hexenoic acid 2-(4-morpholinyl)-ethyl ester, an immunosuppressive glucocorticoid, a polyclonal antibody and a monoclonal antibody.

9. A pharmaceutical composition for use in immunosuppressive therapy in a mammal comprising:
(a) an immunosuppressive agent in a pharmaceutically acceptable carrier and/or excipient, and
(b) at least one compound as defined in claim 1 in a pharmaceutically acceptable carrier and/or excipient, in an amount to produce superadditive immunosuppressant effect.

10. A combination preparation comprising (a) an immunosuppressant agent and (b) at least one compound as defined in claim 1 or a pharmaceutically acceptable salt thereof, in a quantity effective to produce a superadditive immunosuppressive effect for use in a method for lowering the side effects cause by immunosuppressant therapy in a mammal in need thereof.

11. A product comprising a compound as defined in claim 1 and an anti-tumor agent as combined preparation for simultaneous, separate or sequential use in adult-T-cell leukemia-lymphoma therapy.

12. A method of treating a mammal which method comprises administering to said mammal an effective amount of a compound as defined in claim 1 in a pharmaceutically acceptable carrier and/or diluent.

13. A method of treating a mammal suffering from adult-T-cell leukemia-lymphoma, which method comprises administering to said mammal a therapeutically effective amount of a compound as defined in claim 1 in a pharmaceutically acceptable carrier and/or diluent.

14. An immunosuppressive therapy method for use in a mammal in need thereof, which method comprises administering to the mammal (a) an immunosuppressive agent and (b) at least one compound as defined in claim 1, in amounts effective to produce a superadditive immunosuppressive effect.

15. A method according to claim 14 wherein the immunosuppressive agent (a) is selected from at least one member of the group consisting of cyclosporin A, cyclosporin C, FD506, azathioprine, 6-1H-purine, methotrexate, rapamycin, mycophenolate mofetil, 6-(4-hydroxy-6-methoxy-7-methyl-3-oxo-1,3-dihydroisobenzofuran-5-yl)-4-methyl-4-(E)-hexenoic acid 2-(4-morpholinyl)-ethyl ester, an immunosuppressive glucocorticoid, a polyclonal antibody and a monoclonal antibody.

16. A combined method of treatment of adult-T-cell leukemia-lymphoma in a human, in need thereof, which method comprises administering thereto a compound as defined in claim 1, and an anti-tumor agent in an amount sufficient to produce a therapeutically useful effect.

17. A process for the production of a compound as defined in claim 1, which process comprises reacting a compound of formula (II)

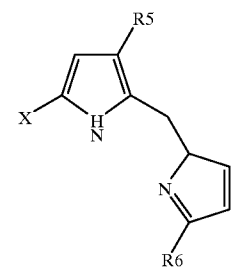

wherein
R5 and R6 are as defined in claim 1 and X is a leaving group, with a compound of formula (III)

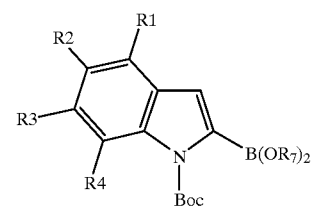

wherein
R1, R2, R3 and R4 are as defined in claim 1 and R7 is hydrogen or a lower alkyl chain; and, if desired, converting a compound of formula (I) into another compound of formula (I) and/or, if desired, salifying a compound of formula (I) and/or, if desired, converting a salt of a compound of formula (I) into a free compound and/or, if desired, separating a mixture of isomers of a compound of formula (I) into the single isomers, where Boc is a 1-tertbutoxycarbonyl group.

18. A compound of formula (III)

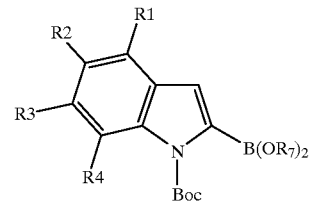

wherein each of
R1, R2, R3 and R4, which are the same or different, independently represents hydrogen, $C_1$–$C_6$ alkyl, halogen, cyano, nitro, hydroxy, $C_1$–$C_6$ alkoxy unsubstituted or substituted by phenyl, $C_1$–$C_6$ alkyl-carbonyloxy, —NraRb in which each of Ra and Rb independently is hydrogen or $C_1$–$C_6$ alkyl, $C_1$–$C_6$ alkyl-carbonylamino, carboxy, ($C_1$–$C_6$ alkoxy) carbonyl, aralkyl-carbamoyl, arylcarbamoyl or —CONRcRd in which each of Rc and Rd independently is hydrogen or $C_1$–$C_6$ alkyl, or Rc and Rd, taken together with the nitrogen atom to which they are linked, form a morpholino or piperidino ring, $R_7$ is hydrogen or a lower alkyl chain, and Boc is a 1-tert-butoxycarbonyl group.

* * * * *

UNITED STATES PATENT AND TRADEMARK OFFICE
CERTIFICATE OF CORRECTION

PATENT NO. : 6,071,947
DATED : June 6, 2000
INVENTOR(S) : Roberto D'Alessio et al.

It is certified that error appears in the above-identified patent and that said Letters Patent is hereby corrected as shown below:

Column 20,
Lines 46 and 47, "2-(5-cyano-1H-indol-2-yl)-4-methoxy-30 2-ylidene)methyl]-1H-pyrrol-2-ylidene)methyl]-1H-pyrrole" should read -- 2-(5-cyano-1H-indol-2-yl)-4-methoxy-5-[(5-undecyl-2H-pyrrol-2-ylidene)methyl]-1H-pyrrole --.

Column 21,
Line 24, "FD506," should read -- FK506 --;
Line 25, "6-1H-purine," should read -- 6-[(1-Methyl-4-nitro-1H-imidazol-5-yl)-thio] 1H-purine --.

Signed and Sealed this

Sixteenth Day of April, 2002

Attest:

JAMES E. ROGAN
Attesting Officer   Director of the United States Patent and Trademark Office